US010407368B2

(12) United States Patent
Karube et al.

(10) Patent No.: US 10,407,368 B2
(45) Date of Patent: Sep. 10, 2019

(54) METHOD FOR PRODUCING HALOOLEFIN COMPOUND AND METHOD FOR REMOVING STABILIZER

(71) Applicant: DAIKIN INDUSTRIES, LTD., Osaka (JP)

(72) Inventors: Daisuke Karube, Osaka (JP); Masayuki Kishimoto, Osaka (JP); Yuzo Komatsu, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/516,504

(22) PCT Filed: Oct. 8, 2015

(86) PCT No.: PCT/JP2015/078573

§ 371 (c)(1),
(2) Date: Apr. 3, 2017

(87) PCT Pub. No.: WO2016/056613

PCT Pub. Date: Apr. 14, 2016

(65) Prior Publication Data

US 2018/0237365 A1 Aug. 23, 2018

(30) Foreign Application Priority Data

Oct. 9, 2014 (JP) ................................ 2014-208123

(51) Int. Cl.
*C07C 17/25* (2006.01)
*C07C 17/20* (2006.01)
*C07C 17/42* (2006.01)
*C07C 17/383* (2006.01)
*C07C 19/01* (2006.01)
*C07C 17/23* (2006.01)
*C07B 61/00* (2006.01)
*C07C 21/18* (2006.01)

(52) U.S. Cl.
CPC ............ *C07C 17/206* (2013.01); *C07C 17/23* (2013.01); *C07C 17/25* (2013.01); *C07C 17/383* (2013.01); *C07C 17/42* (2013.01); *C07B 61/00* (2013.01); *C07C 19/01* (2013.01); *C07C 21/18* (2013.01)

(58) Field of Classification Search
CPC ..................................................... C07C 17/42
See application file for complete search history.

(56) References Cited

U.S. PATENT DOCUMENTS

2011/0130599 A1* 6/2011 Elsheikh .............. C07C 17/206 570/160
2011/0196178 A1* 8/2011 Nyberg ..................... C07C 1/26 570/160
2012/0226081 A1* 9/2012 Elsheikh .............. C07C 17/389 570/239
2014/0275650 A1* 9/2014 Kopkalli .............. C07C 17/202 570/160

FOREIGN PATENT DOCUMENTS

| | | |
|---|---|---|
| JP | 2000-143559 | 5/2000 |
| JP | 2003-26619 | 1/2003 |
| JP | 2003-511226 | 3/2003 |
| JP | 2010-506848 | 3/2010 |
| JP | 2010-534680 | 11/2010 |
| JP | 2011-525925 | 9/2011 |
| WO | 2009/158321 | 12/2009 |
| WO | 2013/065617 | 5/2013 |

OTHER PUBLICATIONS

Iggland, M. et al. "Introduction to Chemical Engineering for Lecture 7: Flash Distillation" 2015, pp. 1-10 (Year: 2015).*
Search Report dated Jun. 19, 2018 in European Application No. 15848172.1.
Office Action dated Jul. 11, 2018 in European Application No. 15848172.1.
International Search Report dated Dec. 28, 2015 in International (PCT) Application No. PCT/JP2015/078573.
Decision to Grant a Patent dated Mar. 25, 2016 in corresponding Japanese Application No. 2014-208123, with translation.
Notification of Reasons for Refusal dated Dec. 16, 2015 in corresponding Japanese Application No. 2014-208123, with translation.
Written Amendment filed Mar. 7, 2016 in corresponding Japanese Application No. 2014-208123, with translation.
Written Argument filed Mar. 7, 2016 in corresponding Japanese Application No. 2014-208123, with translation.

* cited by examiner

*Primary Examiner* — Medhanit W Bahta
(74) *Attorney, Agent, or Firm* — Wenderoth, Lind & Ponack, L.L.P.

(57) ABSTRACT

The present invention provides a method for producing a fluorine-containing haloolefin compound, the method easily inhibiting catalyst deactivation, and the method being capable of inhibiting a decrease in conversion and selectivity in the reaction, even when the reaction is continued for a long period of time. The present invention is a method for producing a fluorine-containing haloolefin compound via a step of fluorinating a $C_3$ halogenated hydrocarbon. The method comprises a step of removing a stabilizer contained in the $C_3$ halogenated hydrocarbon before the fluorination step.

12 Claims, No Drawings

METHOD FOR PRODUCING HALOOLEFIN COMPOUND AND METHOD FOR REMOVING STABILIZER

TECHNICAL FIELD

The present invention relates to a method for producing haloolefin containing a fluorine group, which can be used for a refrigerant etc., and a method for removing a stabilizer.

BACKGROUND ART

Alternative refrigerants such as HFC-125 ($CF_3CHF_2$) and HFC-134a ($CF_3CH_2F$) have been widely used as important replacements for CFC, HCFC, etc., which destroy the ozone layer. However, these alternative refrigerants are potent global warming substances, thus creating concern that their diffusion may affect global warming. To combat this, these refrigerants are collected after use; however, not all of them can be collected, and their diffusion due to, for example, leakage cannot be ignored. Although the use of $CO_2$ or hydrocarbon-based substances as alternative refrigerants has also been studied, $CO_2$ refrigerants have many difficulties in reducing comprehensive greenhouse gas emissions, including energy consumption, because of the requirement of large equipment due to the low efficiency of the $CO_2$ refrigerants. Hydrocarbon-based substances have safety problems due to their high flammability.

Haloolefin compounds containing fluorine groups with a low warming potential are attracting attention as substances that can solve these problems. Known examples of haloolefin compounds containing fluorine groups include 1233xf ($CF_3CCl{=}CH_2$). 1233xf, used alone or in combination with other substances, such as hydrofluorocarbons (HFCs), hydrofluoroolefins (HFOs), and hydrochlorofluoroolefins (HCFOs), is expected to be useful as a refrigerant, and additionally as a blowing agent, propellant, extinguishing agent, or the like. 1233xf is also important as a raw material for producing other hydroolefin compounds such as HFO-1234 yf, which is expected to be used for a refrigerant etc., or as a raw material for producing HCFC-244bb or like other hydrofluoroolefin precursors. Various 1233xf production methods are known. For example, a method in which 1,1,1,2,3-pentachloropropane (240db) or the like is used as a starting material, and reacted with hydrogen fluoride (HF) in the presence of a catalyst is known.

For example, Patent Literature 1 discloses a technique of adding a polymerization inhibitor to 1,1,2,3-tetrachlolopropene in the production of 1233xf and 1,1,1,2-tetrafluoropropene by a reaction of 1,1,2,3-tetrachloropropene and hydrogen fluoride in the presence of a catalyst. By thus adding a polymerization inhibitor as a stabilizer, the lifetime of the catalyst can be extended, thereby increasing the production efficiency of 1233xf and 1,1,1,2-tetrafluoropropene. 1,1,2,3-tetrachloropropene or the like used as a starting material may produce a byproduct by being decomposed or polymerized during storage or reaction. It is assumed that adhesion of the byproduct to the surface of the catalyst deactivates the catalyst. In the technique disclosed in Patent Literature 1, when the starting material is decomposed during storage or reaction, thereby producing an active intermediate such as a radical or an acid component (may be referred to as "radical etc." hereinafter), the radical etc. is captured by a polymerization inhibitor, which serves as a stabilizer. The lifetime of the catalyst can be extended presumably because such capture inhibits a decomposition reaction or a polymerization reaction of the starting material.

CITATION LIST

Patent Literature

PTL 1: JP2011-525925A

SUMMARY OF INVENTION

Technical Problem

However, the examination of the effect of such a stabilizer contained in a halogenated hydrocarbon, such as 1,1,2,3-tetrachloropropene, on the lifetime of a catalyst used in fluorination found that, when the content of the stabilizer exceeds a certain level, the stabilizer itself becomes a cause of shortening the lifetime of the catalyst. Specifically, it was found that, although a stabilizer definitely has an effect of inhibiting decomposition or polymerization reaction of halogenated hydrocarbon, it becomes a cause of deactivating the catalyst when a fluorine-containing haloolefin compound is obtained by fluorination of halogenated hydrocarbon. Further, many commercially available halogenated hydrocarbons generally contain a stabilizer to prevent decomposition or polymerization; however, since the stabilizer can be a cause of deactivating a catalyst in fluorination as described above, it problematically can be a cause of reducing the production efficiency of a target product.

The present invention was accomplished in light of the above problems. An object of the present invention is to provide a method for producing a fluorine-containing haloolefin compound, the method easily inhibiting catalyst deactivation, and the method being capable of inhibiting a decrease in conversion and selectivity in the reaction even when the reaction is continued for a long period of time. Another object of the present invention is to provide a method capable of easily and efficiently removing a stabilizer contained in a $C_3$ halogenated hydrocarbon, which is used as a raw material for producing a haloolefin compound.

Solution to Problem

The inventors of the present invention conducted extensive research to achieve the above objects and found that, in the fluorination of a halogenated hydrocarbon, the above objects can be attained by removing a stabilizer from the halogenated hydrocarbon before the fluorination step. The present invention has thus been accomplished.

Specifically, the present invention relates to the following methods for producing a haloolefin compound.

1. A method for producing a fluorine-containing haloolefin compound via a step of fluorinating a $C_3$ halogenated hydrocarbon, the method comprising the step of removing a stabilizer contained in the $C_3$ halogenated hydrocarbon before the fluorination step.
2. The method according to Item 1, wherein the $C_3$ halogenated hydrocarbon comprises at least one member selected from the group consisting of tetrachloropropenes and pentachloropropanes.
3. The method according to Item 2, wherein the tetrachloropropenes comprise at least one member selected from the group consisting of 1,1,2,3-tetrachloropropene and 2,3,3,3-tetrachloropropene, the pentachloropropanes comprise at least one member selected from the group consisting of 1,1,1,2,3-pentachloropropane and 1,1,2,2,3- pentachloropropane, and the fluorine-containing haloolefin compound comprises 2-chloro-3,3,3-trifluoropropene.

4. The method according to Item 2, wherein the tetrachloropropenes comprise 1,1,3,3-tetrachloropropene, the pentachloropropanes comprise 1,1,1,3,3-pentachloropropane, and the fluorine-containing haloolefin compound comprises 1-chloro-3,3,3-trifluoropropene.
5. The method according to any one of Items 1 to 4, wherein the stabilizer is at least one member selected from the group consisting of aliphatic unsaturated hydrocarbons, hydroxy-containing aromatic compounds, amine compounds, and epoxides.
6. The method according to any one of Items 1 to 5, wherein the content of the stabilizer in the $C_3$ halogenated hydrocarbon is reduced to 100 ppm or less in the step of removing the stabilizer.
7. The method according to any one of Items 1 to 6, wherein the content of the stabilizer in the $C_3$ halogenated hydrocarbon is reduced to 50 ppm or less in the step of removing the stabilizer.
8. The method according to any one of Items 1 to 7, wherein the content of the stabilizer in the $C_3$ halogenated hydrocarbon is reduced to 10 ppm or less in the step of removing the stabilizer.
9. The method according to any one of Items 1 to 8, wherein the step of removing the stabilizer comprises a distillation operation utilizing a difference in boiling point between the stabilizer and the $C_3$ halogenated hydrocarbon.
10. The method according to Item 9, wherein the distillation operation is performed under a reduced pressure less than atmospheric pressure.
11. The method according to Item 9 or 10, wherein the distillation operation and the fluorination are successively performed.
12. The method according to any one of Items 9 to 11; wherein the difference in boiling point between the stabilizer and the $C_3$ halogenated hydrocarbon under atmospheric pressure is 10° C. or more.
13. The method according to Item 12, wherein the difference in boiling point between the stabilizer and the $C_3$ halogenated hydrocarbon under atmospheric pressure is 30° C. or more.
14. A method for removing a stabilizer, comprising the step of removing a stabilizer contained in a $C_3$ halogenated hydrocarbon by distillation, wherein a difference in boiling point between the stabilizer and the $C_3$ halogenated hydrocarbon under atmospheric pressure is 10° C. or more.
15. The method according to Item 14, wherein the difference in boiling point between the stabilizer and the $C_3$ halogenated hydrocarbon under atmospheric pressure is 30° C. or more.
16. The method according to Item 14 or 15, wherein the $C_3$ halogenated hydrocarbon comprises at least one member selected from the group consisting of tetrachloropropenes and pentachloropropanes.
17. The method according to Item 16, wherein the tetrachloropropenes comprise at least one member selected from the group consisting of 1,1,2,3-tetrachloropropene and 2,3,3,3-tetrachloropropene, the pentachloropropanes comprise at least one member selected from the group consisting of 1,1,1,2,3-pentachloropropane and 1,1,2,2,3-pentachloropropane.
18. The method according to Item 16, wherein the tetrachloropropenes comprise 1,1,3,3-tetrachloropropene, and the pentachloropropanes comprise 1,1,1,3,3-pentachloropropane.
19. The method according to any one of Items 14 to 18, wherein the stabilizer is at least one member selected from the group consisting of aliphatic unsaturated hydrocarbons, hydroxy-containing aromatic compounds, amine compounds, and epoxides.
20. The method according to any one of Items 14 to 19, wherein the content of the stabilizer in the $C_3$ halogenated hydrocarbon is reduced to 100 ppm or less by the step of removing the stabilizer.
21. The method according to any one of Items 14 to 19, wherein the content of the stabilizer in the $C_3$ halogenated hydrocarbon is reduced to 50 ppm or less by the step of removing the stabilizer.
22. The method according to any one of Items 14 to 19, wherein the content of the stabilizer in the $C_3$ halogenated hydrocarbon is reduced to 10 ppm or less by the step of removing the stabilizer.

Advantageous Effects of Invention

Since the method for producing a fluorine-containing haloolefin compound of the present invention comprises the step of removing a stabilizer before fluorination of a halogenated hydrocarbon, the amount of the stabilizer contained in the halogenated hydrocarbon is reduced. This prevents deactivation of the catalyst caused by the stabilizer during the fluorination of the halogenated hydrocarbon. As a result, the lifetime of the catalyst is extended, which allows stable reaction for a long period of time. Further, a decrease in conversion of the starting material or a decrease in selectivity of the fluorine-containing haloolefin compound, i.e., the target product, can be prevented even after a long-time reaction, thereby improving production efficiency.

Further, according to the method for removing a stabilizer of the present invention, since the stabilizer contained in the $C_3$ halogenated hydrocarbon is removed by distillation utilizing a difference in boiling point, the stabilizer can be easily isolated and efficiently removed. As is clear from the above, since the removal method described above is thus capable of inhibiting deactivation of the catalyst during the production of the fluorine-containing haloolefin compound, it is possible to improve the production efficiency of the haloolefin compound.

DESCRIPTION OF EMBODIMENTS

Hereinbelow, embodiments of the present invention are described in detail.

In the method for producing a haloolefin compound according to the present embodiment, a fluorine-containing haloolefin compound is produced via a step of fluorinating a $C_3$ halogenated hydrocarbon. In particular, the method for producing a fluorine-containing haloolefin compound according to the present embodiment comprises a step of removing a stabilizer contained in the $C_3$ halogenated hydrocarbon before the step of fluorinating the $C_3$ halogenated hydrocarbon.

The $C_3$ halogenated hydrocarbon (may simply be referred to as "halogenated hydrocarbon" hereinbelow) is a starting material for producing a fluorine-containing haloolefin compound.

The halogenated hydrocarbon is a hydrocarbon having three carbon atoms and at least one halogen as a substituent.

More specifically, the halogenated hydrocarbon is a halogen-substituted propane or a halogen-substituted propene. The halogen-substituted propane is represented by the general formula: $C_3H_aX_{8-a}$, and the halogen-substituted propene is represented by the general formula: $C_3H_bX_{6-b}$, wherein X is halogen, a is an integer of less than 8, and b is an integer of less than 6. The halogen X as a substituent is not particularly limited, and is at least one member selected from the group consisting of fluorine, chlorine, bromine, and iodine. Examples include propane or propene substituted with fluorine, propane or propene substituted with chlorine, as well as propane or propene having both fluorine and chlorine as substituents. The number of halogen atoms as substituents in the halogenated hydrocarbon is not particularly limited.

The halogenated hydrocarbon is preferably at least one member selected from the group consisting of tetrachloropropenes and pentachloropropanes.

The structure of the tetrachloropropenes is not particularly limited. However, 1,1,2,3-tetrachloropropene (hereinbelow simply referred to as "1230xa"), 2,3,3,3-tetrachloropropene (hereinbelow simply referred to as "1230xf"), and 1,1,3,3-tetrachlopropene (hereinbelow simply referred to as "1230za") are preferable.

The structure of the pentachloropropanes is not particularly limited. However, 1,1,1,2,3-pentachloropropane (hereinbelow simply referred to as "240db"), 1,1,2,2,3-pentachloropropane (hereinbelow simply referred to as "240aa"), and 1,1,1,3,3-pentachloropropane (hereinbelow simply referred to as "240fa") are preferable.

The halogenated hydrocarbon may be formed of only one compound, or two or more compounds. As long as the effects of the present invention are not impaired, the starting material may contain a compound other than the halogenated hydrocarbon. Examples of the compounds other than the halogenated hydrocarbon include halogen-unsubstituted $C_3$ hydrocarbons, and halogenated hydrocarbons having a different number of carbon atoms, i.e., having a number of carbon atoms other than 3.

Since the fluorine-containing haloolefin compound is a product obtained by fluorination of the halogenated hydrocarbon mentioned above, the fluorine-containing haloolefin compound may also have 3 carbon atoms. Accordingly, the fluorine-containing haloolefin compound is a halogenated propene having at least a fluorine group as a substituent.

For example, when one or more members selected from the group consisting of 1230xa, 1230xf, 240db, and 240aa are used solely or in combination as the halogenated hydrocarbon as a starting material, the resulting fluorine-containing haloolefin compound contains 2-chloro-3,3,3-trifluoro propene (hereinbelow simply referred to as "1233xf") as a main component.

When one or more members selected from the group consisting of 1230za and 240fa are used solely or in combination as the halogenated hydrocarbon as a starting material, the resulting fluorine-containing haloolefin compound contains 1-chloro-3,3,3-trifluoro propene (hereinbelow simply referred to as "1233zd") as a main component.

Examples of the fluorine-containing haloolefin compound include other compounds. Depending on the kind of the starting material, 2,3,3,3-tetrafluoropropene (hereinbelow simply referred to as "1234yf") or 1,3,3,3-tetrafluoropropene (hereinbelow simply referred to as "1234ze") can be a main component.

The production method according to the present embodiment comprises a step of removing a stabilizer contained in the halogenated hydrocarbon before the fluorination of the halogenated hydrocarbon, which is a starting material. With this removal step, the amount of the stabilizer contained in the halogenated hydrocarbon is reduced. Hereinbelow, this step of removing the stabilizer may simply be referred to as a "removal step."

The stabilizer herein means a substance that is added to inhibit decomposition or polymerization reaction of halogenated hydrocarbons. In general, halogenated hydrocarbons are easily decomposed and active intermediates such as radicals are generated upon decomposition, thereby causing polymerization of the halogenated hydrocarbons with time in some cases. However, when the stabilizer is present in the halogenated hydrocarbon, the stabilizer serves to prevent easy decomposition, or capture the radicals etc. generated by the decomposition. Thus, the decomposition or polymerization reaction of the halogenated hydrocarbons can be inhibited. Accordingly, the stabilizer herein more specifically means a substance capable of inhibiting decomposition of the halogenated hydrocarbons, or a substance having a characteristic allowing itself to capture radicals etc. generated by the decomposition of the halogenated hydrocarbons. Such a stabilizer may also be referred to as an "inhibitor."

Commercially available halogenated hydrocarbons, such as the tetrachloropropenes and pentachloropropanes mentioned above, generally contain the stabilizer described above.

The stabilizer to be removed in the removal step is preferably an aliphatic unsaturated hydrocarbon having a double bond in the molecule, such as amylene (or 1-pentene), d-limonene, and 1-limonene. This aliphatic unsaturated hydrocarbon may be a cyclic or noncyclic compound. Examples of other usable stabilizers include hydroxy-containing aromatic compounds, such as butylhydroxytoluene (also referred to as BHT or 2,6-di-tert-butyl-p-cresol), 4-tert-amylphenol, hydroxyanisole butyrate, 4-methoxy phenol, and hydroquinone; amine compounds such as triethylamine and diisopropylamine; and epoxides. The amine compound may be a cyclic amine compound, such as morpholine. When two or more of the stabilizers listed above are contained, it is preferable to remove at least one stabilizer, and it is more preferable to remove all of the stabilizers.

The stabilizers listed above either have double-bond $\eta$ electrons, a lone pair of nitrogen atom of amino group, or a lone pair of oxygen atom of hydroxy group. Since all of them have an electron-donating property, they presumably strongly adsorb to an acidic catalyst used for fluorination. Therefore, these stabilizers may be considered to be a substance that easily facilitates, in particular, catalyst degradation. From this point of view, it is particularly preferable to remove the stabilizers from the halogenated hydrocarbon. In particular, since an aliphatic unsaturated hydrocarbon having a double bond in the molecule, such as amylene (1-pentene), d-limonene, and 1-limonene, easily deactivates a catalyst, it is particularly preferable to remove and reduce the amounts of these stabilizers.

The method for removing the stabilizer in the removal step is not particularly limited. The separation technique utilizing a property difference between the stabilizer and the halogenated hydrocarbon can be used.

Examples of the method include a method for removing a stabilizer utilizing a difference in melting point or boiling point between the stabilizer and the halogenated hydrocarbon; and a method for removing a stabilizer using a solid adsorbent. When the stabilizer is a solid, a method may be used in which the stabilizer is converted into a liquid by being heated to a melting point of the stabilizer or a higher temperature, after which the stabilizer is removed by distillation or substances other than the stabilizer are removed by distillation. When the stabilizer is a liquid, a method for removing the stabilizer by distillation, or a method in which the stabilizer is isolated by being adsorbed to a solid adsorbent, can be used.

In particular, the stabilizer is preferably removed by distillation utilizing a difference in boiling point between the stabilizer and the halogenated hydrocarbon. In this case, the stabilizer can be easily removed, and the stabilizer can thus be reduced to a desired amount. The pressure in a distillation column for distillation may be normal pressure, reduced pressure, or increased pressure; however, when the distillation is performed under reduced pressure, the heating temperature can be decreased, thereby efficiently performing the removal of the stabilizer.

The separation in the distillation may be performed either continuously or batch-wise. In particular, continuous distillation has an advantage of longtime continuous operation, compared with other separation methods such as a separation method in which a stabilizer is removed by being adsorbed to a solid adsorbent, which requires a regular exchange or reproduction of the solid adsorbent.

When the stabilizer is removed by distillation, if the difference in boiling point between the halogenated hydrocarbon and the stabilizer is small, more distillation steps will be necessary to separate the halogenated hydrocarbon and the stabilizer during the distillation, thereby increasing the size of the distillation column. This may result in an increase in the heating amount of still. Such an excessively large heating amount may promote the decomposition of the halogenated hydrocarbon etc. Since the $C_3$ halogenated hydrocarbon used in the present embodiment has a relatively high boiling point, a large heating amount is basically required compared with distillation using a halogenated hydrocarbon having two or fewer carbon atoms. Thus, it is preferable to increase the difference in boiling point of the stabilizer to be separated, thereby reducing the heating amount as much as possible.

From this point of view, the combination of the halogenated hydrocarbon and the stabilizer is preferably such that the halogenated hydrocarbon and the stabilizer have a boiling point difference of 10° C. or more, more preferably 30° C. or more, in atmospheric pressure.

Preferable examples of such combinations include 1,1,1,2,3-pentachloropropane and amylene; 1,1,1,2,3-pentachloropropane and triethylamine; 1,1,1,2,3-pentachloropropane and diethylamine; 1,1,1,2,3-pentachloropropane, diethylamine, and morpholine; 1,1,1,2,3-pentachloropropane and butylhydroxytoluene (may also be referred to as BHT or 2,6-di-tert-butyl p-cresol); 1,1,1,2,3-pentachloropropane and 4-methoxy phenol; 1,1,1,2,3-pentachloropropane and hydroquinone; 1,1,2,3-tetrachloropropene and amylene; 1,1,2,3-tetrachloropropene and triethylamine; 1,1,2,3-tetrachloropropene and diethylamine; 1,1,2,3-tetrachloropropene and morpholine; 1,1,2,3-tetrachloropropene and butylhydroxytoluene; 1,1,2,3-tetrachloropropene and 4-methoxy phenol; 1,1,2,3-tetrachloropropene and hydroquinone; 1,1,1,3,3-pentachloropropane and amylene; 1,1,1,3,3-pentachloropropane and triethylamine; 1,1,1,3,3-pentachloropropane and diethylamine; 1,1,1,3,3-pentachloropropane and morpholine; 1,1,1,3,3-pentachloropropane and butylhydroxytoluene; 1,1,1,3,3-pentachloropropane and 4-methoxy phenol; and 1,1,1,3,3-pentachloropropane and hydroquinone.

The separation efficiency in the distillation can be increased by thus employing the combination of a halogenated hydrocarbon and a stabilizer having a large boiling point difference in atmospheric pressure as mentioned above (preferably 10° C. or more, more preferably 30° C. or more). This minimizes the decomposition of the halogenated hydrocarbon by distillation.

In performing continuous distillation, for example, a starting material containing a stabilizer is supplied to the middle stage of the distillation column while the isolated stabilizer is removed from the top of the column when the stabilizer has a boiling point lower than that of the raw material; or the isolated stabilizer is removed from the bottom of the column when the stabilizer has a boiling point higher than that of the raw material. When the stabilizer is removed from the top of the column, the starting material is continuously removed from the bottom of the column; and when the stabilizer is removed from the bottom of the column, the starting material is continuously removed from the top of the column. The concentration of the stabilizer in the starting material thus removed from the distillation column is decreased compared with that before distillation. The removed starting material may then be directly supplied to a reactor for performing the fluorination, thereby subsequently performing the distillation and the fluorination. Alternatively, the removed starting material is temporarily stored in a reservoir tank or the like, and then supplied to a reactor for performing the fluorination; this is called a batch-wise method. Since continuous distillation ensures a higher operation efficiency, this method also has an advantage of inhibition of decomposition or polymerization of the halogenated hydrocarbon from which the stabilizer is removed.

By performing the removal step, the amount of the stabilizer contained in the halogenated hydrocarbon can be reduced to, for example, 100 ppm or less, based on the total amount of the halogenated hydrocarbon. As a result, when the halogenated hydrocarbon is used as a raw material of the fluorination, the deactivation of the catalyst used in the fluorination can be inhibited to a greater extent compared with known methods. More specifically, by reducing the amount of the stabilizer in the removal step, the adsorption of the stabilizer to the catalyst can more easily be prevented, thus inhibiting deactivation of the catalyst.

Generally, the halogenated hydrocarbon preferably contains a large amount of stabilizer so as to maintain its storage stability. The halogenated hydrocarbon preferably contains a stabilizer in an amount of about 2 wt % at maximum. However, in some fluorination cases, a stabilizer content of merely 50 ppm or more may decrease the life of the catalyst used in the reaction. From this point of view, in the removal step, the amount of the stabilizer contained in the halogenated hydrocarbon is preferably reduced to 50 ppm or less, particularly preferably 10 ppm or less, based on the total amount of the halogenated hydrocarbon. The stabilizer may be reduced to below the detection limit of gas chromatograph (GC) measurement.

After the removal step, the halogenated hydrocarbon containing a reduced amount of the stabilizer is subjected to fluorination using a catalyst and a fluorinating agent.

Hydrogen fluoride (HF) is preferably used as the fluorinating agent. The catalyst is not particularly limited, and any known catalysts that have been used for fluorination of halogenated hydrocarbon can be used. For example, any known materials that have been traditionally used for such a reaction can be used as catalysts, and the kind thereof is not particularly limited. Examples include halides and oxides of transition metals, elements of group 14, elements of group 15, and the like. In the fluorination, the catalyst may be placed in a reactor beforehand.

Typically, an appropriate amount of the fluorinating agent is about 1 to 100 mol, and about 5 to 50 mol per mol of pentachloropropane and/or tetrachloropropene.

When the fluorinating agent, pentachloropropane, and/or tetrachloropropene is supplied to the reactor, nitrogen, helium, argon, or like inert gas inactivate to the catalyst or the raw material can also be present. When the starting material is supplied to the reactor, an oxidizer, such as oxygen or chlorine, can also be present at the same time.

A tubular reactor is preferably used as the reactor. The contact with the catalyst is preferably performed by a method using a fixed bed. The reactor is preferably made of a material resistant to the corrosive action of the hydrogen fluoride.

The reaction is preferably performed as a gaseous phase reaction in which the effects obtained by reducing the stabilizer are remarkably exhibited. The reaction form etc. is not particularly limited.

The reaction temperature in the fluorination is not particularly limited, and is typically about 200 to 550° C. The pressure in the fluorination is also not particularly limited, and the reaction can be performed under reduced pressure, normal pressure, or increased pressure. The reaction is generally performed under atmospheric pressure (0.1 MPa) or a similar pressure; however, the reaction can be smoothly advanced even under a reduced pressure of less than 0.1 MPa. The reaction may also be performed under an increased pressure to the extent that the raw material is not liquefied.

The reaction time is not limited; however, when a catalyst is used, the contact time represented by W/F0, i.e., the ratio of the catalyst amount W(g) to the total flow rate F0 (a flow rate at 0° C. and 0.1 MPa: cc/sec) of the gas components supplied to the reaction system is preferably about 0.1 to 90 g·sec/cc, and more preferably about 1 to 50 g·sec/cc. When a catalyst is not used, the contact time represented by V/F, i.e., the ratio of the reactor volume V(cc) to the total flow rate F0 (a flow rate at 0° C. and 0.1 MPa: cc/sec) of the gas components supplied to the reaction system is preferably about 0.1 to 100 sec, and more preferably about 1 to 30 sec. In this case, the total flow rate of the gas components means the total flow rate of the raw material, hydrogen fluoride, and hydrogen chloride, as well as, when used, inert gas, oxygen, etc.

Since the production method according to the present embodiment performs the step of reducing the amount of the stabilizer contained in the $C_3$ halogenated hydrocarbon before the fluorination step of the halogenated hydrocarbon, the catalyst used in the fluorination can be prevented from deactivation. Accordingly, even when continuous fluorination is performed, deactivation of the catalyst is not likely to occur even after a long period of time, enabling the fluorination to be stably continued. More specifically, even when the reaction is performed for a long period of time, a decrease in conversion of the starting material, and a decrease in selectivity of the fluorine-containing haloolefin compound, which is the target compound, do not easily occur, thereby improving production efficiency.

Another embodiment of the present invention is a method for removing a stabilizer. The method for removing a stabilizer comprises the step of removing a stabilizer contained in a $C_3$ halogenated hydrocarbon by distillation, wherein the boiling point difference under atmospheric pressure between the stabilizer and the $C_3$ halogenated hydrocarbon is 10° C. or more.

Since this removal method uses a difference in boiling point between the $C_3$ halogenated hydrocarbon and the stabilizer, the stabilizer can be easily and more reliably removed. Thus, the method for removing a stabilizer according to the present embodiment is suitable for purifying the $C_3$ halogenated hydrocarbon, which is a raw material used in the production of the fluorine-containing haloolefin compound. Since the amount of the stabilizer contained in the $C_3$ halogenated hydrocarbon can thus be reduced, deactivation of the catalyst during the production of the fluorine-containing haloolefin compound can be inhibited, thereby improving the efficiency in the production of the fluorine-containing haloolefin compound.

The difference in boiling point under atmospheric pressure between the stabilizer and the $C_3$ halogenated hydrocarbon is preferably 30° C. or more. In this case, the amount of the stabilizer can be further reduced. The type and preferable form of the $C_3$ halogenated hydrocarbon, the type and preferable form of the stabilizer, the preferable range of the amount of the stabilizer after removal, and the like in the method for removing a stabilizer are similar to those in the production method described above.

EXAMPLES

Hereinafter, the present invention is more specifically explained with reference to Examples; however, the present invention is not limited to these Examples.

Example 1

In the following manner, amylene contained as a stabilizer in 1,1,1,2,3-pentachloropropane (hereinbelow simply referred to as "240db"), which is a $C_3$ halogenated hydrocarbon, was removed by distillation, and 2-chloro-3,3,3-trifluoropropene (1233xf) was produced using the resulting 240db from which the stabilizer was removed.

First, a starting material containing 1200 ppm of amylene relative to 240db ($CCl_3CHClCH_2Cl$) was prepared. The amylene used herein was a stabilizer added as an inhibitor for inhibiting the decomposition of 240db. The amount of the stabilizer contained in the starting material was reduced by distillation by performing the removal step. More specifically, 400 g of the starting material was introduced into a 500-ml volume still in a distillation column. After the atmospheric pressure in the distillation column was reduced to 30 mmHg, the still was heated to perform distillation. When the temperature at the top of the column was increased to 90 to 92° C. by heating, 5 g of a fore-running fraction containing amylene was separated, and then 240db was collected until distillation ceased. The amount and the yield of collected 240db were 360 g and 90%. The content of amylene according to the gas chromatograph (GC) analysis was 10 ppm or less.

Fluorination was performed under a gaseous phase in the following manner using 240db in which the content of the stabilizer was reduced by the removal step. First, 10.0 g of a chrome oxide catalyst was placed in a tubular Hastelloy reactor having a length of 1 m. The reactor tube was heated, and the catalyst was fluorinated using hydrogen fluoride gas.

Subsequently, the temperature of the reactor tube was increased to 300° C., and anhydrous hydrogen fluoride gas was supplied to the reactor at a flow rate of 60.0 Nml/min, and maintained for 0.5 hours. Thereafter, 240 db gas was supplied at a flow rate of 3.0 Nml/min. About 10 hours afterward, the gas discharged from the reactor was analyzed using a gas chromatograph (GC), thereby determining the conversion of 240db, which is a starting material, and the selectivity of 1233xf, which is a generated fluorine-containing haloolefin compound. The results revealed that the conversion of 240db was 100% and the selectivity of 1233xf was 98% at a time point 10 hours after the start of the reaction. Further, even 80 hours after the start of the reaction, the conversion of 240db was kept at 100% and the selectivity of 1233xf was kept at 98%.

Example 2

In the following manner, butylhydroxytoluene (hereinbelow simply referred to as "BHT") contained as a stabilizer in 240db was removed by distillation, and 1233xf was produced using 240db from which the stabilizer was removed.

First, a starting material containing 1200 ppm of BHT relative to 240db was prepared. BHT used herein was a stabilizer added as an inhibitor for inhibiting the decomposition of 240db. The amount of the stabilizer contained in the starting material was reduced by distillation by performing the removal step. More specifically, 400 g of the starting material was introduced into a 500-ml volume still in a distillation column. After the atmospheric pressure in the distillation column was reduced to 30 mmHg, the still was heated to perform distillation. When the temperature at the top of the column was increased to 90 to 92° C. by heating, 240db was collected until distillation ceased. The amount and the yield of collected 240db were 355 g and 89%. The content of BHT according to the gas chromatograph (GC) analysis was 10 ppm or less.

Fluorination was performed under a gaseous phase in the same method as in Example 1 using 240db in which the content of the stabilizer was reduced by the removal step. The conversion of 240db and the selectivity of generated 1233xf were analyzed. The results revealed that the conversion of 240db was 100% and the selectivity of 1233xf was 98% at a time point 10 hours after the start of the reaction. Further, even 80 hours after the start of the reaction, the conversion of 240db was kept at 100% and the selectivity of 1233xf was kept at 98%.

Example 3

The amount of amylene contained as a stabilizer in 240db was reduced to 50 ppm by the removal step. Fluorination was performed under a gaseous phase in the same method as in Example 1 using the resulting 240db. The conversion of 240db and the selectivity of generated 1233xf were analyzed. The results revealed that the conversion of 240db was 100% and the selectivity of 1233xf was 98% at a time point 10 hours after the start of the reaction. Further, even 80 hours after the start of the reaction, the conversion of 240db was 99% and the selectivity of 1233xf was kept at 91%.

Comparative Example 1

240db containing amylene in an amount of 200 ppm or less was prepared, and fluorination was performed under a gaseous phase using the 240db in the same method as in Example 1, without performing the removal step of Example 1. The conversion of 240db and the selectivity of generated 1233xf were analyzed. The results revealed that the conversion of 240db was 100% and the selectivity of 1233xf was 98% at a time point 10 hours after the start of the reaction. Further, 80 hours after the start of the reaction, the conversion of 240db was decreased to 94% and the selectivity of 1233xf was decreased to 84%.

Comparative Example 2

Fluorination was performed under a gaseous phase using 240db containing amylene in an amount of 1200 ppm in the same method as in Example 1, without performing the removal step. The conversion of 240db and the selectivity of generated 1233xf were analyzed. The results revealed that the conversion of 240db and the selectivity of 1233xf were rapidly decreased compared with those of Comparative Example 1.

In the production methods of Examples 1 to 3, the fluorination was performed by reducing the amount of the stabilizer contained in the $C_3$ halogenated hydrocarbon by performing the removal step. Therefore, even when the reaction was continued for a long period of time, the conversion of 240db and the selectivity of 1233xf were kept at a high level. In particular, it was revealed that the smaller the amount of the stabilizer, the greater the conversion and the selectivity. In contrast, when the fluorination was performed with a large amount of stabilizer as in Comparative Examples 1 and 2 without performing the step of removing the stabilizer, the conversion of 240db and the selectivity of 1233xf were greatly decreased over the reaction time.

The above results clearly revealed that, by reducing the amount of the stabilizer by performing the removal step, deactivation of the catalyst by the stabilizer can be inhibited; and that, consequently, the conversion and the selectivity were kept at a high level, even when the fluorination was continued for a long period of time.

The invention claimed is:

1. A method for producing a fluorine-containing haloolefin compound via a step of fluorinating a $C_3$ halogenated hydrocarbon, wherein the $C_3$ halogenated hydrocarbon comprises at least one member selected from the group consisting of tetrachloropropenes and pentachloropropanes, the method comprising the step of removing a stabilizer contained in the $C_3$ halogenated hydrocarbon before the fluorination step, wherein the stabilizer is at least one member selected from the group consisting of an aliphatic unsaturated hydrocarbon having a double bond in the molecule, an amine compound, and an epoxide, wherein the amine compound is at least one member selected from the group consisting of triethylamine, diisopropylamine, and a cyclic amine compound, and wherein the stabilizer is contained in such an amount as to affect degradation of a catalyst for use in the fluorination of the $C_3$ halogenated hydrocarbon.

2. The method according to claim 1, wherein the tetrachloropropenes comprise at least one member selected from the group consisting of 1,1,2,3-tetrachloropropene and 2,3,3,3-tetrachloropropene, the pentachloropropanes comprise at least one member selected from the group consisting of 1,1,1,2,3-pentachloropropane and 1,1,2,2,3-pentachloropropane, and the fluorine-containing haloolefin compound comprises 2-chloro-3,3,3-trifluoropropene.

3. The method according to claim 1, wherein the tetrachloropropenes comprise 1,1,3,3-tetrachloropropene, the pentachloropropanes comprise 1,1,1,3,3-pentachloropropane, and the fluorine-containing haloolefin compound comprises 1-chloro-3,3,3-trifluoropropene.

4. The method according to claim 1, wherein a content of the stabilizer in the $C_3$ halogenated hydrocarbon is reduced to 100 ppm or less by the step of removing the stabilizer.

5. The method according to claim 1, wherein a content of the stabilizer in the $C_3$ halogenated hydrocarbon is reduced to 50 ppm or less by the step of removing the stabilizer.

6. The method according to claim 1, wherein a content of the stabilizer in the $C_3$ halogenated hydrocarbon is reduced to 10 ppm or less by the step of removing the stabilizer.

7. The method according to claim 1, wherein the amine compound is morpholine.

8. A method for producing a fluorine-containing haloolefin compound via a step of fluorinating a $C_3$ halogenated hydrocarbon, wherein the $C_3$ halogenated hydrocarbon comprises at least one member selected from the group consisting of tetrachloropropenes and pentachloropropanes, the method comprising the step of removing a stabilizer contained in the $C_3$ halogenated hydrocarbon before the fluorination step, wherein the stabilizer is at least one member selected from the group consisting of an aliphatic unsaturated hydrocarbon having a double bond in the molecule, an amine compound, and an epoxide, wherein the stabilizer is contained in such an amount as to affect degradation of a catalyst for use in the fluorination of the $C_3$ halogenated hydrocarbon, and wherein the step of removing the stabilizer comprises a distillation operation utilizing a difference in boiling point between the stabilizer and the $C_3$ halogenated hydrocarbon.

9. The method according to claim 8, wherein the distillation operation is performed under a reduced pressure less than atmospheric pressure.

10. The method according to claim 9, wherein the distillation operation and fluorination are successively performed.

11. The method according to claim 8, wherein the difference in boiling point between the stabilizer and the $C_3$ halogenated hydrocarbon under atmospheric pressure is 10° C. or more.

12. The method according to claim 11, wherein the difference in boiling point between the stabilizer and the $C_3$ halogenated hydrocarbon under atmospheric pressure is 30° C. or more.

* * * * *